(12) United States Patent
Huang et al.

(10) Patent No.: US 10,041,080 B2
(45) Date of Patent: Aug. 7, 2018

(54) MODIFIED PROMOTER SEQUENCE AND APPLICATION THEREOF

(71) Applicant: Yuan Ze University, Taoyuan (TW)

(72) Inventors: Li-Fen Huang, Taoyuan (TW); Peng-Wen Chen, Chiayi (TW); Su-May Yu, Taipei (TW)

(73) Assignee: YUAN ZE UNIVERSITY, Taoyuan (TW)

(*) Notice: Subject to any disclaimer, the term of this patent is extended or adjusted under 35 U.S.C. 154(b) by 594 days.

(21) Appl. No.: 14/600,472

(22) Filed: Jan. 20, 2015

(65) Prior Publication Data
US 2016/0017353 A1    Jan. 21, 2016

(30) Foreign Application Priority Data
Jul. 21, 2014 (TW) .............................. 103124951 A

(51) Int. Cl.
*C12N 15/82* (2006.01)
(52) U.S. Cl.
CPC ................................ *C12N 15/8222* (2013.01)
(58) Field of Classification Search
None
See application file for complete search history.

(56) References Cited

U.S. PATENT DOCUMENTS

| | | | | |
|---|---|---|---|---|
| 6,288,302 B1* | 9/2001 | Yu | ................ | C12N 15/8222 |
| | | | | 435/429 |
| 2003/0135884 A1* | 7/2003 | Yu | ................ | C12N 15/8245 |
| | | | | 800/284 |
| 2011/0283377 A1* | 11/2011 | Mirkov | ............. | C12N 15/8222 |
| | | | | 800/260 |

OTHER PUBLICATIONS

Wu et al (The modified rice αAmy8 promoter confers high-level foreign gene expression in a novel hypoxia-inducible expression system in transgenic rice seedlings. Plant Mol Biol 85:147-161, 2014. Published online Jan. 21, 2014)*
Chen et al (Interaction between Rice MYBGA and the Gibberellin Response Element Controls Tissue-Specific Sugar Sensitivity of a-Amylase Genes. The Plant Cell, vol. 18, 2326-2340, Sep. 2006)*
Wu et al (Disruption of YPS1 and PEP4 genes reduces proteolytic degradation of secreted HSA/PTH in Pichia pastoris GS115. J Ind Microbiol Biotechnol 40:589-599, 2013).*

* cited by examiner

*Primary Examiner* — Medina A Ibrahim
*Assistant Examiner* — Wayne Zhong
(74) *Attorney, Agent, or Firm* — WPAT, PC

(57) ABSTRACT

The present invention relates to a modified plant promoter and applications using the same, including an expression construct comprising the promoter for expressing a gene of interest in a plant expression system. In particular, the present invention relates to a method for producing a polypeptide by expressing a plant cell transformed with the expression construct and recovering the polypeptide from the culture. The present invention also relates to a method for producing a polypeptide by growing a transgenic plant transformed with the expression construct and recovering the polypeptide from the transgenic plant.

20 Claims, 5 Drawing Sheets

SEQUENCE LISTING

<160> NUMBER OF SEQ ID NOS: 15

<210> SEQ ID NO 1
<211> LENGTH: 1174
<212> TYPE: DNA
<213> ORGANISM: Artificial Sequence
<220> FEATURE:
<223> OTHER INFORMATION: promoter

<400> SEQUENCE: 1

| | | | | | |
|---|---|---|---|---|---|
| cggaggacta | gcgaagaata | ctgcagctgg | ggttggcgct | gctaatgacc | aacgtttgat | 60 |
| cattcgtttt | atttattttt | tttgtaaata | tgaaaatatt | tatgtcatgt | ttaaagaaca | 120 |
| tttgatgatg | aatcaagtca | caataaaaga | aaaataatt | gcataatttt | ttttaaataa | 180 |
| aaagaatgat | caaacgttaa | acaaaaagtc | aacgtcatac | attaaaacat | aaaagttagt | 240 |
| ataattcaaa | gatatggatg | aaggtcacaa | gcaatgcgct | tgacgtggtg | caaatctgga | 300 |
| gttattgagc | tttccattgc | atgtctgtga | ttttaccaag | tcaatcgacg | tttgctgttt | 360 |
| tctttgcaaa | tagtcctaga | ctaagttact | tgcagttgca | ggattatggt | ggattggtga | 420 |
| cggagttggt | gcttatggcc | tttgtttct | gtcaggggag | ttgtctgctc | tgcaggtcat | 480 |
| ataaactctg | taaagtgta | tattggcatt | tcgtcgatga | aatgggagag | gatctcctct | 540 |
| ctttttcaa | taaaaaaag | taaatgcaaa | atatatgtcc | gttgcaccga | tctccttcc | 600 |
| aaaccgaaag | tttccctgcc | ggcgcttgat | ccgtcacacc | gatgacgcga | cgccggtaga | 660 |
| ggcccggtac | ctgttcgaac | aaccaactga | tgtgcggctc | ctccgcttgc | ggcttgcctc | 720 |
| ttatcaacgt | atcgcgaatt | cccgggtgcg | tgatcggtga | tcgatcaccg | agagagaccg | 780 |
| gacgacgagt | cgagagagct | cgcgcgcgcc | tcgatcggcg | cggcggtgac | tcgacctacg | 840 |
| tggcaagtag | ctgcacggct | caaggcggca | ctccatcacc | ggacaccggg | gtccagacta | 900 |
| ctcgtttccg | ttggagaaat | aaccatcctt | atccatatcc | acgccccggg | aattgcaaca | 960 |
| gcattgattg | ttgatatcta | attcgcctcg | gccatgtaac | ctccgacctg | atcctcttgg | 1020 |
| acactataaa | tagaggccag | ttcaggcaat | gcaagagcag | agaagcagag | tcgaccaggc | 1080 |
| agctcttctt | ctctttgcga | aggttggcta | cttggccagc | cattaggaaa | caagttagtt | 1140 |
| tggagaagaa | gcagagttga | gactgcattt | gcat | | | 1174 |

<210> SEQ ID NO 2
<211> LENGTH: 1050
<212> TYPE: DNA
<213> ORGANISM: Zea mays

<400> SEQUENCE: 2

```
agatctcccc caaatccacc cgtcggcacc tccgcttcaa ggtacgccgc tcgtcctccc      60 ccccccccc tctctacctt ctctagatcg gcgttccggt ccatggttag ggcccggtag      120
ttctacttct gttcatgttt gtgttagatc cgtgtttgtg ttagatccgt gctgctagcg      180
ttcgtacacg gatgcgacct gtacgtcaga cacgttctga ttgctaactt gccagtgttt      240
ctctttgggg aatcctggga tggctctagc cgttccgcag acgggatcga tttcatgatt      300 tttttgttt cgttgcatag ggtttggttt gcccttttcc tttatttcaa tatatgccgt      360
gcacttgttt gtcgggtcat cttttcatgc ttttttttgt cttggttgtg atgatgtggt      420
ctggttgggc ggtcgttcta gatcggagta gaattctgtt tcaaactacc tggtggattt      480
attaattttg gatctgtatg tgtgtgccat acatattcat agttacgaat gaagatgat       540 ggatggaaat atcgatctag gataggtata catgttgatg cgggttttac tgatgcatat      600
acagagatgc tttttgttcg cttggttgtg atgatgtggt gtggttgggc ggtcgttcat      660
tcgttctaga tcggagtaga atactgtttc aaactacctg gtgtatttat taattttgga      720
actgtatgtg tgtgtcatac atcttcatag ttacgagttt aagatggatg gaaatatcga      780
tctaggatag gtatacatgt tgatgtgggt tttactgatg catatacatg atggcatatg      840
cagcatctat tcatatgctc taaccttgag tacctatcta ttataataaa caagtatgtt      900
ttataattat tttgatcttg atatacttgg atgatggcat atgcagcagc tatatgtgga      960
tttttttagc cctgccttca tacgctattt atttgcttgg tactgtttct tttgtcgatg     1020
ctcaccctgt tgtttggtgt tacttctgca                                      1050

<210> SEQ ID NO 3
<211> LENGTH: 96
<212> TYPE: DNA
<213> ORGANISM: Oryza sativa

<400> SEQUENCE: 3
atgaagaaca ccagcagctt gtgtttgctg ctcctcgtgg tgctctgcag cttgacctgt      60
aactcgggtc aagcacaggt cctcttcgat aagctt                                96

<210> SEQ ID NO 4
<211> LENGTH: 2337
<212> TYPE: DNA
<213> ORGANISM: artificial sequence
<220> FEATURE:
<223> OTHER INFORMATION: Promoter+Ubi+SP

<400> SEQUENCE: 4
cggaggacta gcgaagaata ctgcagctgg ggttggcgct gctaatgacc aacgtttgat      60
cattcgtttt atttattttt tttgtaaata tgaaaatatt tatgtcatgt ttaaagaaca     120
tttgatgatg aatcaagtca caataaaaga aaaataatt gcataatttt tttaaataa      180 aaagaatgat caaacgttaa acaaaaagtc aacgtcatac attaaaacat aaaagttagt     240
ataattcaaa gatatggatg aaggtcacaa gcaatgcgct tgacgtggtg caaatctgga     300
gttattgagc tttccattgc atgtctgtga ttttaccaag tcaatcgacg tttgctgttt     360
tctttgcaaa tagtcctaga ctaagttact tgcagttgca ggattatggt ggattggtga     420
cggagttggt gcttatggcc tttgtttct gtcaggggag ttgtctgctc tgcaggtcat     480
ataaactctg taaagtgta tattggcatt tcgtcgatga atgggagag gatctccctct    540 cttttttcaa taaaaaaag taaatgcaaa atatatgtcc gttgcaccga tctccttccc    600
```

| | |
|---|---:|
| aaaccgaaag tttccctgcc ggcgcttgat ccgtcacacc gatgacgcga cgccggtaga | 660 |
| ggcccggtac ctgttcgaac aaccaactga tgtgcggctc ctccgcttgc ggcttgcctc | 720 |
| ttatcaacgt atcgcgaatt cccgggtgcg tgatcggtga tcgatcaccg agagagaccg | 780 |
| gacgacgagt cgagagagct cgcgcgcgcc tcgatcggcg cggcggtgac tcgacctacg | 840 |
| tggcaagtag ctgcacggct caaggcggca ctccatcacc ggacaccggg gtccagacta | 900 |
| ctcgtttccg ttggagaaat aaccatcctt atccatatcc acgccccggg aattgcaaca | 960 |
| gcattgattg ttgatatcta attcgcctcg gccatgtaac ctccgacctg atcctcttgg | 1020 |
| acactataaa tagaggccag ttcaggcaat gcaagagcag agaagcagag tcgaccaggc | 1080 |
| agctcttctt ctctttgcga aggttggcta cttggccagc cattaggaaa caagttagtt | 1140 |
| tggagaagaa gcagagttga gactgcattt gcatagatct cccccaaatc cacccgtcgg | 1200 |
| cacctccgct tcaaggtacg ccgctcgtcc tcccccccc ccctctcta ccttctctag | 1260 |
| atcggcgttc cggtccatgg ttagggcccg gtagttctac ttctgttcat gtttgtgtta | 1320 |
| gatccgtgtt tgtgttagat ccgtgctgct agcgttcgta cacggatgcg acctgtacgt | 1380 |
| cagacacgtt ctgattgcta acttgccagt gtttctcttt ggggaatcct gggatggctc | 1440 |
| tagccgttcc gcagacggga tcgatttcat gatttttttt gtttcgttgc atagggtttg | 1500 |
| gtttgccctt ttccttttatt tcaatatatg ccgtgcactt gtttgtcggg tcatcttttc | 1560 |
| atgcttttt ttgtcttggt tgtgatgatg tggtctggtt gggcggtcgt tctagatcgg | 1620 |
| agtagaattc tgtttcaaac tacctggtgg atttattaat tttggatctg tatgtgtgtg | 1680 |
| ccatacatat tcatagttac gaattgaaga tgatggatgg aaatatcgat ctaggatagg | 1740 |
| tatacatgtt gatgcgggtt ttactgatgc atatacagag atgcttttttg ttcgcttggt | 1800 |
| tgtgatgatg tggtgtggtt gggcggtcgt tcattcgttc tagatcggag tagaatactg | 1860 |
| tttcaaacta cctggtgtat ttattaattt tggaactgta tgtgtgtgtc atacatcttc | 1920 |
| atagttacga gtttaagatg gatggaaata tcgatctagg ataggtatac atgttgatgt | 1980 |
| gggtttttact gatgcatata catgatggca tatgcagcat ctattcatat gctctaacct | 2040 |
| tgagtaccta tctattataa taaacaagta tgtttataa ttattttgat cttgatatac | 2100 |
| ttggatgatg gcatatgcag cagctatatg tggattttttt tagccctgcc ttcatacgct | 2160 |
| atttatttgc ttggtactgt ttcttttgtc gatgctcacc ctgttgtttg gtgttacttc | 2220 |
| tgcagactag tttacacaga tatgaagaac accagcagct tgtgtttgct gctcctcgtg | 2280 |
| gtgctctgca gcttgacctg taactcgggt caagcacagg tcctcttcga taagctt | 2337 |

<210> SEQ ID NO 5
<211> LENGTH: 53
<212> TYPE: PRT
<213> ORGANISM: Homo sapiens

<400> SEQUENCE: 5

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

```
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Val Pro
            405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
            485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Gly Lys Lys Leu Val
            565                 570                 575
Ala Ala Ser Gln Ala Ala Leu Gly Leu
            580                 585

<210> SEQ ID NO 7
<211> LENGTH: 1932
<212> TYPE: DNA
<213> ORGANISM: Artificial Sequence
<220> FEATURE:
<223> OTHER INFORMATION: H-EGF fused sequence

<400> SEQUENCE: 7
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca agacatcc ttacttttat gccccggaac tccttttctt tgctaaaagg      480
tataaagctg cttttacaga atgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag gcggaccctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
```

```
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc ttttttgagca gcttggagag   1200
tacaaattcc agaatgcgct attagttcgt tacaccaaga agtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca gcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc aaggcaaca   1620
aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttaggatc catcgagggc cgcaactccg actccgagtg cccgctctcc   1800
cacgacggct actgcctcca cgacggcgtg tgcatgtaca tcgaggccct cgacaagtac   1860
gcctgcaact gcgtggtggg ctacatcggc gagcgctgcc agtaccgcga cctcaagtgg   1920
tgggagctcc gc                                                       1932

<210> SEQ ID NO 8
<211> LENGTH: 4269
<212> TYPE: DNA
<213> ORGANISM: artificial sequence
<220> FEATURE:
<223> OTHER INFORMATION: promoter+Ubi+SP+H-EGF

<400> SEQUENCE: 8
cggaggacta gcgaagaata ctgcagctgg ggttggcgct gctaatgacc aacgtttgat     60
cattcgtttt atttattttt tttgtaaata tgaaaatatt tatgtcatgt ttaaagaaca    120
tttgatgatg aatcaagtca caataaaaga aaaataatt gcataatttt ttttaaataa    180
aaagaatgat caaacgttaa acaaaaagtc aacgtcatac attaaaacat aaaagttagt    240
ataattcaaa gatatggatg aaggtcacaa gcaatgcgct tgacgtggtg caaatctgga    300
gttattgagc tttccattgc atgtctgtga ttttaccaag tcaatcgacg tttgctgttt    360
tctttgcaaa tagtcctaga ctaagttact tgcagttgca ggattatggt ggattggtga    420
cggagttggt gcttatggcc tttgtttttct gtcaggggag ttgtctgctc tgcaggtcat    480
ataaactctg taaagtgta tattggcatt tcgtcgatga atgggagag atctcctct    540
ctttttcaa taaaaaag taatgcaaa atatatgtcc gttgcaccga tctccttcc    600
aaaccgaaag tttccctgcc ggcgcttgat ccgtcacacc gatgacgcga cgccggtaga    660
ggcccggtac ctgttcgaac aaccaactga tgtgcggctc ctccgcttgc ggcttgcctc    720
ttatcaacgt atcgcgaatt cccgggtgcg tgatcggtga tcgatcaccg agagagaccg    780
gacgacgagt cgagagagct cgcgcgcgcc tcgatcggcg cggcggtgac tcgacctacg    840
tgcaagtag ctgcacggct caaggcggca ctccatcacc ggacaccggg gtccagacta    900
ctcgtttccg ttgagaaaat aaccatcctt atccatatcc acgccccggg aattgcaaca    960
gcattgattg ttgatatcta attcgcctcg gccatgtaac ctccgacctg atcctcttgg   1020
```

```
acactataaa tagaggccag ttcaggcaat gcaagagcag agaagcagag tcgaccaggc    1080
agctcttctt ctctttgcga aggttggcta cttggccagc cattaggaaa caagttagtt    1140
tggagaagaa gcagagttga gactgcattt gcatagatct cccccaaatc cacccgtcgg    1200
cacctccgct tcaaggtacg ccgctcgtcc tccccccccc ccctctctct ccttctctag    1260
atcggcgttc cggtccatgg ttagggcccg gtagttctac ttctgttcat gtttgtgtta    1320
gatccgtgtt tgtgttagat ccgtgctgct agcgttcgta cacggatgcg acctgtacgt    1380
cagacacgtt ctgattgcta acttgccagt gtttctcttt ggggaatcct gggatggctc    1440
tagccgttcc gcagacggga tcgatttcat gatttttttt gtttcgttgc atagggtttg    1500
gtttgccctt ttcctttatt tcaatatatg ccgtgcactt gtttgtcggg tcatcttttc    1560 atgcttttt ttgtcttggt tgtgatgatg tggtctggtt gggcggtcgt tctagatcgg    1620
agtagaattc tgtttcaaac tacctggtgg atttattaat tttggatctg tatgtgtgtg    1680
ccatacatat tcatagttac gaattgaaga tgatggatgg aaatatcgat ctaggatagg    1740
tatacatgtt gatgcgggtt ttactgatgc atatacagag atgcttttg ttcgcttggt    1800 tgtgatgatg tggtgtggtt gggcggtcgt tcattcgttc tagatcggag tagaatactg    1860
tttcaaacta cctggtgtat ttattaattt tggaactgta tgtgtgtgtc atacatcttc    1920
atagttacga gtttaagatg gatggaaata tcgatctagg ataggtatac atgttgatgt    1980
gggttttact gatgcatata catgatggca tatgcagcat ctattcatat gctctaacct    2040
tgagtaccta tctattataa taaacaagta tgttttataa ttattttgat cttgatatac    2100
ttggatgatg gcatatgcag cagctatatg tggattttt tagccctgcc ttcatacgct    2160
atttatttgc ttggtactgt ttctttttgtc gatgctcacc ctgttgtttg tgttacttc    2220 tgcagactag tttacacaga tatgaagaac accagcagct tgtgtttgct gctcctcgtg    2280
gtgctctgca gcttgacctg taactcgggt caagcacagg tcctcttcga taagcttgat    2340
gcacacaaga gtgaggttgc tcatcggttt aaagatttgg gagaagaaaa tttcaaagcc    2400
ttggtgttga ttgcctttgc tcagtatctt cagcagtgtc catttgaaga tcatgtaaaa    2460
ttagtgaatg aagtaactga atttgcaaaa acatgtgttg ctgatgagtc agctgaaaat    2520
tgtgacaaat cacttcatac cctttttgga gacaaattat gcacagttgc aactcttcgt    2580
gaaacctatg gtgaaatggc tgactgctgt gcaaaacaag aacctgagag aaatgaatgc    2640
ttcttgcaac acaaagatga caacccaaac ctcccccgat tggtgagacc agaggttgat    2700
gtgatgtgca ctgcttttca tgacaatgaa gagacatttt tgaaaaaata cttatatgaa    2760
attgccagaa gacatcctta cttttatgcc ccggaactcc ttttctttgc taaaaggtat    2820
aaagctgctt ttacagaatg ttgccaagct gctgataaag ctgcctgcct gttgccaaag    2880
ctcgatgaac ttcgggatga agggaaggct tcgtctgcca acagagact caagtgtgcc    2940 agtctccaaa aatttggaga aagagctttc aaagcatggg cagtagctcg cctgagccag    3000
agatttccca agctgagtt tgcagaagtt tccaagttag tgacagatct taccaaagtc    3060
cacacggaat gctgccatgg agatctgctt gaatgtgctg atgacagggc ggaccttgcc    3120
aagtatatct gtgaaaatca agattcgatc tccagtaaac tgaaggaatg ctgtgaaaaa    3180
cctctgttgg aaaaatccca ctgcattgcc gaagtggaaa atgatgagat gcctgctgac    3240
ttgccttcat tagctgctga ttttgttgaa agtaaggatt tttgcaaaaa ctatgctgag    3300
gcaaaggatg tcttcctggg catgttttg tatgaatatg caagaaggca tcctgattac    3360
```

-continued

```
tctgtcgtgc tgctgctgag acttgccaag acatatgaaa ccactctaga gaagtgctgt    3420
gccgctgcag atcctcatga atgctatgcc aaagtgttcg atgaatttaa acctcttgtg    3480
gaagagcctc agaatttaat caaacaaaat tgtgagcttt ttgagcagct tggagagtac    3540
aaattccaga atgcgctatt agttcgttac accaagaaag tacccccaagt gtcaactcca   3600 actcttgtag aggtctcaag aaacctagga aaagtgggca gcaaatgttg taaacatcct    3660
gaagcaaaaa gaatgccctg tgcagaagac tatctatccg tggtcctgaa ccagttatgt    3720
gtgttgcatg agaaaacgcc agtaagtgac agagtcacca aatgctgcac agaatccttg    3780
gtgaacaggc gaccatgctt ttcagctctg gaagtcgatg aaacatacgt tcccaaagag    3840
tttaatgctg aaacattcac cttccatgca gatatatgca cactttctga aaggagaga    3900 caaatcaaga aacaaactgc acttgttgag ctcgtgaaac acaagcccaa ggcaacaaaa    3960
gagcaactga aagctgttat ggatgatttc gcagcttttg tagagaagtg ctgcaaggct    4020
gacgataagg agacctgctt tgccgaggag ggtaaaaaac ttgttgctgc aagtcaagct    4080
gccttaggct taggatccat cgagggccgc aactccgact ccgagtgccc gctctcccac    4140
gacggctact gcctccacga cggcgtgtgc atgtacatcg aggccctcga caagtacgcc    4200
tgcaactgcg tggtgggcta catcggcgag cgctgccagt accgcgacct caagtggtgg    4260
gagctccgc                                                            4269
```

```
<210> SEQ ID NO 9
<211> LENGTH: 38
<212> TYPE: DNA
<213> ORGANISM: artificial sequence
<220> FEATURE:
<223> OTHER INFORMATION: primter 2TAF

<400> SEQUENCE: 9
ccttatccat atccacgcgc cccgggaatt gcaacagc                              38

<210> SEQ ID NO 10
<211> LENGTH: 18
<212> TYPE: DNA
<213> ORGANISM: artificial sequence
<220> FEATURE:
<223> OTHER INFORMATION: primer Luc1

<400> SEQUENCE: 10
tccagcggtt ccatcctc                                                   18

<210> SEQ ID NO 11
<211> LENGTH: 34
<212> TYPE: DNA
<213> ORGANISM: Artificial Sequence
<220> FEATURE:
<223> OTHER INFORMATION: primter GboxF1

<400> SEQUENCE: 11
gtgagtcgac ctacgtggca agtagctgca cggc                                 34

<210> SEQ ID NO 12
<211> LENGTH: 19
<212> TYPE: DNA
<213> ORGANISM: Artificial Sequence
<220> FEATURE:
<223> OTHER INFORMATION: primer HSA-forward

<400> SEQUENCE: 12
gggcatgttt ttgtatgaa                                                  19
```

```
<210> SEQ ID NO 13
<211> LENGTH: 20
<212> TYPE: DNA
<213> ORGANISM: Artificial Sequence
<220> FEATURE:
<223> OTHER INFORMATION: primer HSA-reverse

<400> SEQUENCE: 13
ttataagcct aaggcagctt                                              20

<210> SEQ ID NO 14
<211> LENGTH: 20
<212> TYPE: DNA
<213> ORGANISM: Artificial Sequence
<220> FEATURE:
<223> OTHER INFORMATION: primer Actin-forward

<400> SEQUENCE: 14
ctgatggaca ggttatcacc                                              20

<210> SEQ ID NO 15
<211> LENGTH: 22
<212> TYPE: DNA
<213> ORGANISM: Artificial Sequence
<220> FEATURE:
<223> OTHER INFORMATION: Primer Actin-reverse

<400> SEQUENCE: 15
caggtagcaa taggtattac ag                                           22
```

MODIFIED PROMOTER SEQUENCE AND APPLICATION THEREOF

RELATED APPLICATIONS

This application claims the benefit of Taiwan Patent Application No. TW103124951, filed on Jul. 21, 2014, the entire content of which is incorporated herein by reference.

TECHNOLOGY FIELD

The present invention relates to a modified promoter and applications using the same, including an expression construct comprising the promoter for expressing a gene of interest and a method for producing a polypeptide using the expression construct, particularly in a plant expression system.

BACKGROUND OF THE INVENTION

Plant-based expression systems have been increasingly used in producing proteins, because of a variety of advantages over the conventional expression system in bacterial or animal cells. For example, plants are capable of producing proteins in a large scale at low cost, plants do not contain animal pathogens that may cause contamination in the final protein product, and plant cells provide eukaryotic post translational processing that may be necessary for proper biological function of proteins. Examples of recombinant proteins that have been produced in plants include therapeutic proteins such as insulin, interferons, epidermal growth factors and immunoglobulins and industrial enzymes such as xylanase.

A promoter is a sequence of DNA that can initiate the transcription of a gene. A number of promoters which are active in plant cells have been described in the literature, including the cauliflower mosaic virus (CaMV) 35S promoter, the *commelina* yellow mottle virus promoter, the rice cytosolic triosephosphate isomerase (TPI) promoter, the rice actin 1 (Act1) gene promoter, the uniquitin (Ubi) promoter, the rice amylase gene promoter, the adenine phosphoribosyltransferase (APRT) promoter of *Arabidopsis*, the mannopine synthase and octopine synthase promoters.

There is a continue need for a modified promoter exhibiting strong activity for high-level expression of introduced genes, especially in plant cells.

BRIEF SUMMARY OF THE INVENTION

In one aspect, the present invention provides a modified promoter, comprising the sequence as set forth in SEQ ID NO: 1.

In another aspect, the present invention provides a recombinant construct, comprising an expression cassette which comprises a regulatory sequence, operatively linked to a nucleotide sequence encoding a polypeptide of interest, wherein the regulatory sequence comprises the promoter having the sequence as set forth in SEQ ID NO: 1 as described herein.

The present invention also provides a transformed cell or a transgenic plant comprising the recombinant construct as described herein.

The present invention further provides a method for producing a polypeptide comprising:
(a) culturing a cell transformed with the recombinant construct as describe herein under a condition for expression of the polypeptide; and
(b) recovering the polypeptide from the culture.

In one certain embodiment, the method of the invention is conducted in plant cells and the polypeptide as expressed is recovered from suspension culture of the transformed plant cells, particularly from the culture medium. In one example, the plant cells are from rice.

The present invention further provides a method for producing a polypeptide comprising:
(a) growing a transgenic plant containing the recombinant construct as describe herein under a condition suitable for expression of the polypeptide of interest; and
(b) recovering the polypeptide from the transgenic plant.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments which are presently preferred. It should be understood, however, that the invention is not limited to the illustrated preferred embodiments. In the drawings.

DETAILED DESCRIPTION OF THE INVENTION

Figure 1:
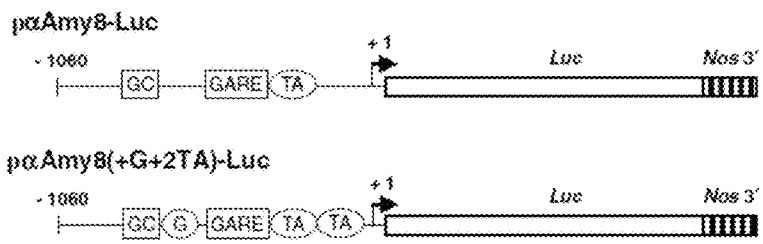
FIG. 1 shows that the modified αAmy8 promoter containing the G box and duplicated TA box confers significantly higher luciferase activity in transgenic rice cells and seedlings. (A) Schematic representation of constructs for αAmy8 and αAmy8 (+G+2TA) promoter analysis. (B) T0 transformed rice suspension cells carrying the αAmy8::Luc gene or the αAmy8 (+G+2TA)::Luc gene were cultured in sucrose containing (+sucrose, open bar) or sucrose-free (−sucrose, filled bar) MS liquid medium for 2 days. Cells were collected and luciferase activity was determined Error bars indicate the SE of luciferase activity readings from five independently transformed rice cell lines for each construct. (C) T2 seeds of homozygous transgenic lines Amy8-16-6 and Amy8(+G+2TA)-5-2 carrying the αAmy8::Luc and αAmy8(+G+2TA)::Luc chimeric genes, respectively, were germinated and grown for 7 days. Endosperm (filled bar), embryo (dotted bar), shoot (hatched bar), and root (open bar) were collected daily from ten germinating seeds or seedlings of each transgenic line and then pooled and for luciferase activity assay. Error bars indicate the SE.
Figure 1:
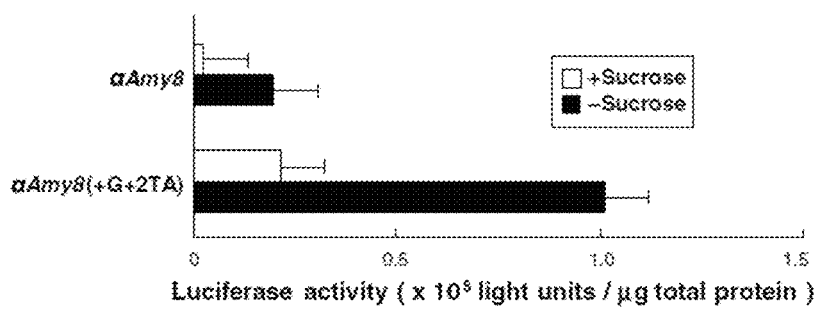
Figure 1:
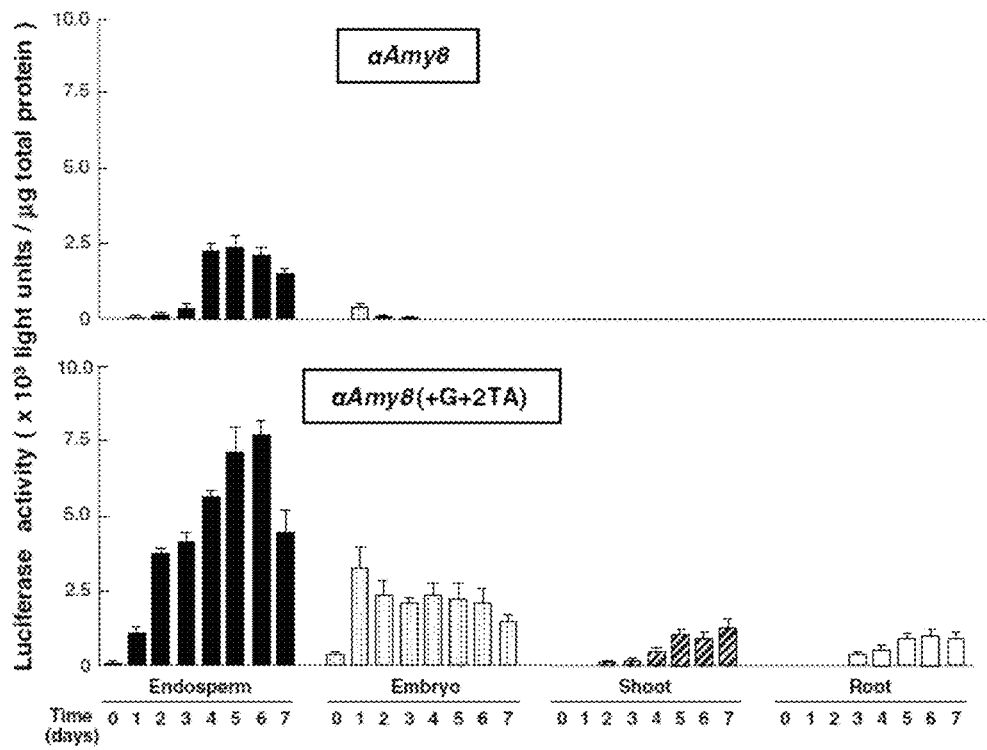

Unless defined otherwise, all technical and scientific terms used herein have the same meanings as is commonly understood by one of skill in the art to which this invention belongs. If a conflict appears, one should base on this document, including the definitions therein.

As used herein, the articles "a" and "an" refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant construct" refers to a polynucleotide or nucleic acid having sequences that are not naturally joined together. A recombinant construct may be present in the form of a vector. "Vectors" may contain an expression cassette comprising a given nucleotide sequence of interest and a regulatory sequence operatively linked thereto so that the given nucleotide sequence can be transcribed and optionally translated. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above mentioned purposes. A "recombinant cell" refers to a cell that has had introduced into it a recombinant nucleic acid.

As used herein, the term "operatively linked" may mean that a polynucleotide is linked to an expression control sequence in such a manner to enable expression of the polynucleotide when a proper molecule (such as a transcriptional factor) is bound to the expression control sequence.

As used herein, the term "regulatory sequence" or "expression control sequence" means a DNA sequence that regulates the expression of the operatively linked nucleic acid sequence in a certain host cell.

Examples of vectors include, but are not limited to, plasmids, cosmids, phages, YACs or PACs. For plant, a binary vector for *Agrobacterium*-mediated DNA transfer is preferred, which includes a modified T-region from Ti plasmid, allowing replication in both *E. coli* and *Agrobacterium* cells. Examples of a binary vector include but are not limited to pPZP and pCAMBIA series.

Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., cytomegalovirus (CMV) promoter, simian virus 40 (SV40) early promoter, T7 promoter, and alcohol oxidase gene (AOX1) promoter, and those particularly suitable in plant expression system such as Figwort mosaic virus 35S promoter, cauliflower mosaic virus (CaMV) 35S promoter, *commelina* yellow mottle virus promoter, rice cytosolic triosephosphate isomerase (TPI) promoter, rice actin 1 (Act1) gene promoter, rice amylase gene promoter, adenine phosphoribosyltransferase (APRT) promoter of *Arabidopsis*, mannopine synthase and octopine synthase promoters), a start codon, a replication origin, enhancers (e.g. a uniquitin (Ubi) enhancer, a Cowpea Mosaic Virus (CPMV) 5'UTR, and plastocyanin 3' UTR), an operator sequence, a secretion signal sequence (e.g., a-mating factor signal and αAmy3 signal peptide sequence) and other control sequence (e.g., termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

To prepare a transgenic plant, it is preferably that the expression vector as used herein carries one or more selection markers for selection of the transformed plants, for example, genes conferring the resistance to antibiotics such as hygromycin, ampicillin, gentamycine, chloramphenicol, streptomycin, kanamycin, neomycin, geneticin and tetracycline, URA3 gene, genes conferring the resistance to any other toxic compound such as certain metal ions or herbicide, such as glufosinate or bialaphos.

As used herein, the term "transgenic plant" or "transgenic line" refers to a plant that contains a recombinant nucleotide sequence that encodes a gene i.e. a transgene. The transgenic plant can be grown from a recombinant cell.

A variety of procedures that can be used to engineer a stable transgenic plant are available in this art. In one embodiment of the present invention, the transgenic plant is produced by transforming a tissue of a plant, such as a protoplast or leaf-disc of the plant, with a recombinant construct *Agrobacterium* cell comprising a polynucleotide encoding a desired protein (e.g. epidermal growth factor, EGF) and generating a whole plant from the transformed plant tissue. In another embodiment, a polynucleotide encoding a desired protein can be introduced into a plant via gene gun technology, particularly if transformation with a recombinant *Agrobacterium* cell is not efficient in the plant.

Expression systems may be used to express a protein of interest in a host organism by recombinant technology. As used herein, a gene encoding a protein of interest to be expressed in a host organism, for example, present in a recombinant construct, operatively linked to a regulatory sequence, may be deemed as an "exogenous" gene, because it is not naturally present in a given host genome, although the protein itself as encoded may be endogenous or heterologous to the host organism. In plant, a designed expression vector can be introduced to plant cells for expression of a protein of interest. In general, transformed plant cells are cultured in a suitable medium with selective agent e.g. antibiotics and the transformed plant cells with suitable selection markers which are survived in the medium can be selected for regeneration of plants. Once callus forms, shoot formation can be promoted by using proper plant hormones and the shoots are transferred to rooting medium for regeneration of plants in accordance with known methods in the art. The plants may then be used to establish repetitive generations, such as from seeds or using vegetative propagation techniques. Plant cells suitable in the present invention may be from seeds, calli, flowers, root, stems, leaves and cultured cell suspensions. According to the invention, the expression system is preferably applied in higher plants, such as rice, corn, barley, potatoes, tomatoes, cotton, sugar beets and carrots.

The term "polypeptide" refers to a polymer composed of amino acid residues linked via peptide bonds. The term "protein" typically refers to relatively large polypeptides. The term "peptide" typically refers to relatively short polypeptides.

The amino acid sequence of the polypeptide described herein may include its biological equivalent, which means that there is a limited number of changes or modifications that may be made within a certain portion of the molecule irrelevant to the activity or function of the protein and still result in a molecule with an substantially the same level of the biological activity. Biologically equivalent polypeptides are thus defined herein as those polypeptides in which certain amino acid residues may be substituted. Polypeptides with different substitutions may be made and used in accordance with the invention. Modifications and changes may be made in the structure of such polypeptides and still obtain a molecule having similar or desirable characteristics. For example, certain amino acids may be substituted for other amino acids in the peptide/polypeptide structure without appreciable loss of activity Amino acid substitutions are generally based on the relative similarity of the amino acid side-chain substituents, for example, their hydrophobicity, hydrophilicity, charge, size, and the like. For example, arginine (Arg), lysine (Lys), and histidine (His) are all positively charged residues; and alanine (Ala), glycine (Gly) and serine (Ser) are all in a similar size. Therefore, based upon these considerations, arginine (Arg), lysine (Lys) and histidine (His); and alanine (Ala), glycine (Gly) and serine (Ser) may be defined as biologically functional equivalents. One can readily design and prepare recombinant genes for microbial expression of polypeptides having equivalent amino acid residues.

In the present invention, it is unexpected found that a newly designed promoter sequence, which is made by modifying a conventional αAmy8 promoter by specifically insertion of one G box adjacent to GC box and duplication of TA box, having the nucleotide sequence as set forth in SEQ ID NO: 1, confers significantly enhanced promoter activity and can be used in development of more production-efficient protein expression system.

Therefore, in one aspect, the present invention provides a modified promoter comprising the nucleotide sequence as set forth in SEQ ID NO: 1.

In another aspect, the present invention provides a recombinant construct, comprising an expression cassette which comprises a regulatory sequence, operatively linked to a nucleotide sequence encoding a polypeptide, wherein the regulatory sequence comprises a promoter having the nucleotide sequence as set forth in SEQ ID NO: 1 as described herein.

In some embodiments, the regulatory sequence can further comprise an enhancer to increase the transcriptional efficacy. In a certain example, the enhancer is a uniquitin (Ubi) intron sequence, having the nucleotide sequence of SEQ ID NO: 2.

In some embodiments, the regulatory sequence can further comprise a signal peptide sequence to ensure secretion of the recombinant protein. In a certain example, the signal peptide sequence is derived from αAmy3, having the nucleotide sequence of SEQ ID NO: 3.

In some embodiments, the regulatory sequence comprises a promoter of SEQ ID NO: 1, a Ubi intron sequence of SEQ ID NO: 2 and a signal peptide sequence of SEQ ID NO: 3. In a certain example, the regulatory sequence comprises the nucleotide sequence of SEQ ID NO: 4 (the promoter and Ubi plus SP).

According to the present invention, a regulatory sequence comprising a promoter sequence of SEQ ID NO: 1 is operatively linked to a nucleotide sequence encoding a polypeptide of interest to form an expression cassette which can be included in an expression vector. The expression vector may contain other elements such as a selection marker and a terminator. Vectors suitable to introduce the inventive polynucleotide into plant cells include a Ti plasmid, a root-inducing (Ri) plasmid and a plant virus vector. Examples of the suitable vectors include, but are not limited to, binary vectors, such as pPZP and pCAMBIA series. Persons skilled in the art can choose a vector suitable to introduce the polynucleotide of the invention into a plant.

In some embodiments, a polypeptide of interest to be expressed in the expression system as described herein can be a therapeutic protein such as epidermal growth factor (EGF). In certain embodiments, the EGF is from human, having the amino acid sequence of SEQ ID NO: 5. Preferably, the EGF is fused with human serum albumin (HSA, SEQ ID NO: 6) to improve stability. In a specific example, a nucleotide sequence encoding a fusion polypeptide of EGF and HSA (i.e. H-EGF), having the nucleotide sequence of SEQ ID NO: 7, is operatively linked to a regulatory sequence comprising the promoter sequence of SEQ ID NO: 1 as described above to form an expression cassette. The expression cassette can be included in a suitable vector to form a recombinant construct.

A recombinant construct can be introduced into cells using any method known in the art. Thus, the present invention provides a recombinant cell transformed with the construct of the invention. A protein of interest can be prepared by culturing a recombinant cell transformed with the recombinant construct in a suitable condition and conducting purification by methods known in the art.

Accordingly, the present invention provides a method for producing a polypeptide comprising (a) culturing a cell transformed with the recombinant construct as described herein and (b) recovering the polypeptide from the culture. Expression of a recombinant protein in transformed cells may be monitored or confirmed by a method known in the art e.g. western blotting.

In certain embodiments, the method of invention is applied in plant cells. Specifically, a transformed plant cell in accordance of the invention is used to regenerate of a transgenic plant. The regenerated plants can be transferred to soil conditions and cultivated in a conventional manner. Preferably, a stable line that contains the expression cassette of the invention in a stable manner and optionally more than one copy of the introduced nucleotide sequence encoding a protein of interest such that high levels of expression of said protein may be achieved, is selected. Optionally, a breeding program may be contemplated such that other plant strains or varieties having the desired coding sequence of a protein of interest may be obtained for example, by a program of controlled backcrossing. It is possible to generate parental lines comprising the coding sequence of a protein of interest included in the expression cassette of the invention and all plants in subsequent generations from the parental lines. The present invention provides all plant parts, such as seeds, comprising the coding sequence of a protein of interest included in the expression cassette of the invention, from which such plant parts can be grown and the resultant tissue cultures such as callus, protoplasts, seedlings or cell suspensions are generated which can be used in protein expression or can be generated back to plants.

In particular embodiments of the invention, suspension cultures are generated and the expressed protein is collected from the suspension cultures, preferably from the culture medium. The expressed protein can also be collected from the plant parts e.g. seedlings by protein extraction through cell lysis.

In particular embodiments of the invention, plant cells are cultured in a sugar deficient condition under hypoxia (e.g. in water). A sugar deficient condition can mean a condition where the concentration of sugar such as sucrose is zero or substantially lower than a normal condition, for example, being 50%, 40%, 30%, 20%, or 10% of the sugar concentration in a normal sugar containing medium (10-30 g/L). A hypoxia condition may mean a deprivation of oxygen supply, where the concentration of oxygen is zero or substantially lower than a normal condition, for example being 50%, 40%, 30%, 20%, or 10% of the oxygen concentration in the atmosphere (20%), such as under water.

In particular embodiments of the invention, a transgenic plant having the recombinant construct as described herein, which comprises the coding sequence of a protein of interest to be expressed, are grown under a condition suitable for expression of the protein of interest, and then the expressed protein is recovered from the transgenic plant e.g. via extraction. Specifically, the transgenic plant used for protein expression can be directly generated from plant cells transformed with the recombinant construct of the invention or grown from plant seeds of parent transgenic lines. As a certain example, plant seeds of transgenic lines of the invention are germinated, resultant seedlings are grown under a condition suitable for expression of the protein of interest and collected, and the protein of interest is harvested from the seedlings by extraction.

The present invention is further illustrated by the following examples, which are provided for the purpose of demonstration rather than limitation.

EXAMPLES

1. Materials and Methods 1.1 Plant Materials

The rice variety used for genetic transformation in this study was *Oryza sativa* L. cv. Tainung 67. Immature seeds were de-hulled, sterilized with 3% sodium hypochlorite for 30 min, washed extensively with sterile water, and placed on N6D agar medium (Toki S (1997). *Plant Mol Biol Rep* 5:16-21) for callus induction. After 1 month of culture, calli derived from scutellum were sub-cultured in fresh N6D medium for transformation.

1.2 Plasmids

Plasmid p8SRC/GARC-4 (pαAmy8SRC/GARC-Luc) contains αAmy8 SRC/GARC (−318 to −89) fused to CaMV35S minimal promoter (−46 bp from the transcription start site), upstream of Adh1 intron, Luc coding sequence, and nopaline synthase gene (Nos) terminator (Chen et al. (2006). *Plant Cell* 18 (9):2326-2340). Plasmid pUG contains β-glucuronidase (GUS) cDNA in between maize Ubi promoter and Nos terminator (Christensen and Quail (1996). Transgenic Res 5 (3):213-218). Plasmid pAHC18 contains Ubi promoter and Luc cDNA (Bruce et al. (1989). *Proc Natl Acad Sci USA* 86 (24):9692-9696). Plasmid p35 mA-Luc contains the CaMV35S minimal promoter and Luc cDNA (Lu et al. (1998) *J Biol Chem* 273 (17):10120-10131).

1.3 Plasmid Construction

PCR-based oligonucleotide-directed mutagenesis approach was used for modification of the cis-acting elements in SRC/GARC (Picard et al. (1994). *Nucleic acids research* 22 (13):2587-2591).

1.4 Transformation of Rice

Plasmid pA8(+G+2TA) was introduced into *Agrobacterium tumefaciens* strain EHA101 (Hood et al. (1986). *J Bacteriol* 168 (3):1291-1301) with an MicroPulser electroporator (Bio-Rad) following the manufacturer's instruction. Rice transformation was performed as described previously (Chen et al. (2002). *J Biol Chem* 277 (16):13641-13649). Transformed rice calli were selected on N6 medium that contained 50 mg/L of hygromycin.

1.5 Rice Embryo Transient Expression Assay

Rice seeds were sterilized and incubated in liquid MS medium containing 2 µg/ml 2,4-dichlorophenoxyacetic acid (2,4-D) at 28° C. After incubation for 8 days, the embryos were dissected and then placed with the scutellar side up on the same medium solidified with 0.3% (w/v) Phytagel (Sigma). Particle bombardment of the rice embryo in transient expression assay was performed as described previously (Umemura et al. (1998) *Planta* 204 (4):420-428). Bombarded rice embryos were incubated in liquid MS medium containing 100 mM glucose or mannitol at 28° C. for 24 hours. In each independent experiment 8 embryos were used and performed in three replicates. Luciferase and GUS activity were determined and the internal control (Ubi:GUS) was used for data normalization as described previously (Chen et al. (2006). supra).

1.6 Luciferase and GUS Activity Assay

Total cellular proteins were extracted from bombarded rice embryos, various tissues, or cultured suspension cells with CCLR buffer (100 mM $KH_2(PO_4)$, pH 7.8, 1 mM EDTA, 10% glycerol, 1% Triton X-100, 7 mM β-mercaptoethanol) and the protein concentration was determined with Coomassie Brilliant Blue R 250 protein assay reagent (Pierce). Luciferase and GUS activity assays were performed as previously described (Lu et al. (1998) supra).

1.7 Suspension Cell Culture

Transformed calli were propagated as previously described (Yu et al. (1991) *J Biol Chem* 266 (31):21131-21137). Established suspension cells were sub-cultured as previously described (Lu et al. (1998) *J Biol Chem* 273 (17):10120-10131). The embryo-containing portion of rice grain was removed by excision and the resultant grain was sterilized with 1% NaOCl and one drop of Tween 20 for about 60 min and then watered with sterile water for three times, each for about 20 min. The grain was placed with scutellum side up on agar medium and incubated at 28° C. under 24-hour light illumination for three weeks. The resultant calli were transferred to a liquid medium in a 125 ml flask. The suspension culture was incubated at 28° C. under 24-hour light illumination with shaking (100 rpm).

1.8 Seed Germination or Seedling Growth in Air or Under Submerged Conditions Rice seeds were sterilized with 3% NaOCl and rinsed with sterile distilled water. For germination in air, seeds were placed on 1% (w/v) solidified agar-water in test tube. For germination under water, seeds were placed in a test tube as in germination in the air experiment and the test tube was placed in the bottom of a 2 L graduated cylinder filled with 45 cm of autoclaved water. Subsequently, seeds were allowed to germinate in distilled water at 28° C. in the dark at indicated time points. Aerobic and hypoxic tissues were collected from 10 rice seedlings and the samples were pooled and assayed for luciferase activity or Western blotting. For seedlings grown under water, seeds were germinated and grown in ½ MS medium with 3% sucrose in a test tube for 7 days at 28° C. in a 14-hour light (7000 lux)/10-hour dark cycle. Seven-day-old seedlings were incubated in air or under submerged conditions in the ½ MS medium with or without 3% sucrose at 28° C. for 7 days in the dark. Aerobic and hypoxic seedlings were collected and assayed for luciferase activity. The water in the cylinders was not circulated or refreshed during the treatment. Oxygen concentration in the water in the cylinders was determined by a dissolved oxygen meter (Model EcoScan DO6, Eutech Instruments Pte. Ltd.). The $O_2$ concentration in water declines to <0.03 mol $m^{-3}$ after 7 days under submergence treatments.

1.9 Protein Gel Blot Analysis

Total cellular proteins were extracted from cultured rice suspension cells, aerobic and hypoxic rice seedlings with CCLR buffer. Expression of recombinant hEGF in transgenic rice cells and seedlings were analyzed by protein gel blot analysis as described previously (Lu et al. (2007) *Plant Cell* 19 (8):2484-2499. doi:tpc.105.037887), except that the total soluble proteins were electrophoresed in 16% Tris-tricine SDS-PAGE and the gel was electroblotted to a 0.2 µm nitrocellulose membrane. The hEGF fusion protein was detected with anti-HSA polyclonal antibody (1:1000, Abcam) or anti-hEGF monoclonal antibody (1:500, R&D Systems).

1.10 Cell Proliferation Assay

The biological activity of recombinant hEGF produced by transgenic rice cells and seedlings was analyzed by human kidney-2 (HK-2) cell proliferation assay described in Sarkozi et al. (2007) *J Cell Physiol* 211 (1):88-100. HK-2 cells were grown in keratinocyte-serum free medium K-SFM (Gibco BRL) supplemented with 5 ng/ml of commercial EGF and incubated at 37° C. in a 5% $CO_2$ humidified incubator. Cells were sub-cultured at a ratio of 1:3 every 2 or 3 days. For measurement of cell proliferation, HK-2 cells were carefully washed with PBS three times and resuspended in serum-free K-SFM. Cells were then plated in six-well plates (Falcon) at a concentration of $1 \times 10^5$ cells/ml serum-free K-SFM per well. After 48 hours of incubation at 37° C., the medium was refreshed and HK-2 cells were stimulated with 150 ng/ml of total rice secretary protein from the suspension cells of rice cultivars TNG67 (non-transformed rice cell) or H-EGF rice cell line (containing 5 ng/ml H-EGF proteins), or 5 ng/ml of commercial EGF on day 0 and 2. Cells from triplicate wells were trypsinized, stained with 0.2% trypan blue and counted on day 0, 2, and 4 using a hemacytometer for three times. Same treatments were applied to a human bone marrow neuroblastoma cell line, SH-SY5Y, and a rat lung epithelial cell line, L2.

2. Results

2.1 Construction of Modified αAmy8 Promoter of the Invention

For the construction of plasmid carrying modified αAmy8 SRS/GARS with the G box and the duplicated TA box in the αAmy8 promoter, the 5'-flanking region (−1060 to +127) of αAmy8 was excised from pAG8 (Chan et al., (1993) *Plant Mol Biol* 22:491-506) by HindIII and NcoI and the restriction fragment was sub-cloned into p35 mA-Luc, yielding pαAmy8-Luc. The TA box in αAmy8 was duplicated in a two-stage PCR as described above using 2TAF (5'-CCT-TATCCATATCCACGCGCCCCGGGAATTGCAACAGC-3' (SEQ ID NO:

9)) and Luc 1 (5'-TCCAGCGGTTCCATCCTC-3' (SEQ ID NO: 10)) primers as the forward and reverse primers, respectively, and pαAmy8-Luc as the DNA template in the first PCR. The PCR product was used as the reverse megaprimer in the second PCR with T3 primer as the forward primer. The PCR fragment containing the duplicated TA box of αAmy8 promoter was then sub-cloned into p35 mA-Luc in between HindIII and NcoI, generating pαAmy8(+2TA)-Luc. The G box and the duplicated TA box in αAmy8 promoter was modified by PCR using GboxF1 (5'-GTGAGTCGAC-CTACGTGGCAAGTAGCTGCACGGC-3' (SEQ ID NO: 11)) and Luc 1 primer as the forward and reverse primers, respectively, and pαAmy8(+2TA)-Luc as the DNA template in the first PCR. The PCR product was then used as the reverse megaprimer in the second PCR with T3 primer as the forward primer and pαAmy8(+2TA)-Luc as the DNA template. The DNA fragment containing the G box and the duplicated TA box of αAmy8 promoter was then sub-cloned into p35 mA-Luc at HindIII and NcoI, generating pαAmy8(+G+2TA)-Luc. See FIG. 1(A), the lower panel. The engineered promoter of the invention (pαAmy8(+G+2TA) having the nucleotide sequence of SEQ ID NO: 1 was confirmed by DNA sequencing.

2.2 Promoter Activity Assay

The 1-kb αAmy8 promoter of the invention, i.e. pαAmy8(+G+2TA), containing the G box and duplicated TA box, was fused upstream of luciferase gene, generating αAmy8(+G+2TA)::Luc (FIG. 1A). The chimeric gene was introduced into the rice genome, and five independently transformed cell lines of each construct were randomly selected and cultured as suspension cells. The luciferase activity assay was conducted and the result shows that the αAmy8(+G+2TA) promoter conferred up to 10- and 5-fold higher luciferase activities, in the presence and absence of sucrose, respectively, as compared with the wild-type αAmy8 promoter (FIG. 1B). The αAmy8(+G+2TA) promoter also conferred higher luciferase activity, peaked at day 5-6, by approximately 4-fold, than the wild-type αAmy8 promoter in various tissues of transgenic seedlings (FIG. 1C). The results demonstrate that the αAmy8 promoter of the invention can be applied in plant expression system for high level production of foreign proteins.

2.3 the αAmy8(+G+2TA) Promoter Exhibits Significantly Higher Luciferase Activity in Transgenic Rice Seedlings Under Water.

Figure 2:
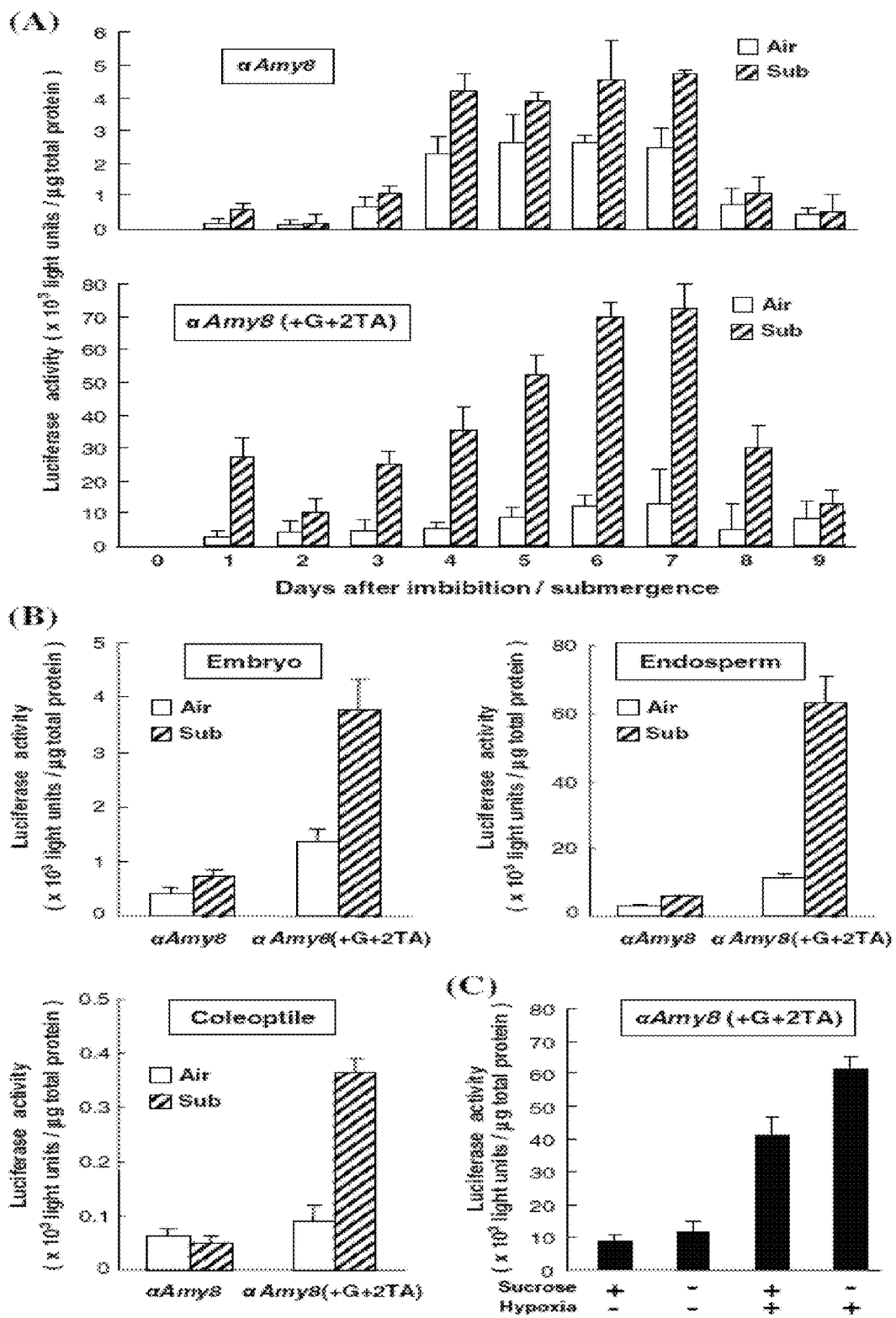
FIG. 2 shows that the αAmy8(+G+2TA) promoter exhibits significantly higher luciferase activity in transgenic rice seedlings under water. T2 seeds of homozygous transgenic lines Amy8-16-6 and Amy8(+G+2TA)-5-2 carrying the αAmy8::Luc gene and αAmy8(+G+2TA)::Luc gene, respectively, were germinated and grown in air (Air) or under water (Sub) for up to 9 days. (A) Ten aerobic or hypoxic seedlings of each transgenic line were collected daily. (B) Embryos, endosperms, and coleoptiles were collected and assayed for luciferase activity on day 7. (C) T2 seeds of transgenic line Amy8(+G+2TA)-5-2 were germinated and grown in air (Hypoxia, "−") or under water (Hypoxia, "+") with (+) or without (−) sucrose for 7 days, and luciferase activity was determined Error bars indicate the SE.

The effectiveness of the G box and duplicated TA box in enhancing the αAmy8 promoter activity under hypoxia was then determined Both the wild-type αAmy8 and αAmy8(+G+2TA) promoter activities peaked on 6-7 days after germination, but the absolute activity and inducibility of αAmy8(+G+2TA) promoter by hypoxia was significantly higher than the wild-type promoter (FIG. 2A). The fold induction of the αAmy8(+G+2TA) promoter by hypoxia was similar in embryo, endosperm, and coleoptile, but its absolute activity was significantly higher in endosperm (FIG. 2B). The αAmy8(+G+2TA) promoter conferred high hypoxia-inducible activity regardless of whether seedlings were incubated with or without sucrose (FIG. 2C). Taken together, these results demonstrate that the G box and duplicated TA box significantly enhance the αAmy8 promoter activity in all rice tissues, particularly under sugar starvation and hypoxia.

2.4 Application of αAmy8(+G+2TA) Promoter in EGF Recombinant Protein Expression in Rice To determine whether the modified αAmy8 could direct high-level accumulation of foreign human proteins in rice, an expression construct comprising the recombinant human epidermal growth factor (EGF) gene operatively linked to downstream of the αAmy8(+G+2TA) promoter, ubi intron1 and signal peptide of αAmy3 was prepared and introduced into rice cells for expression. The results show that EGF proteins were detected in transformed rice suspension cells (data not shown).

Figure 3:
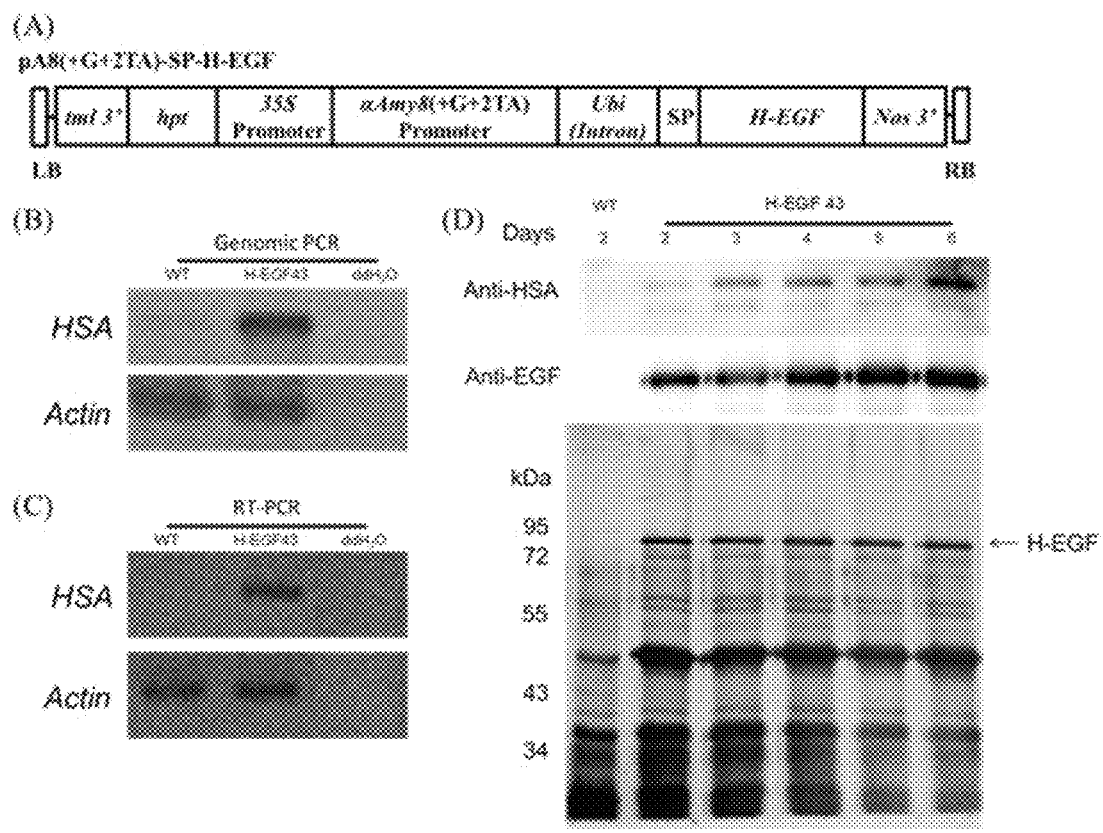
FIG. 3 shows that the expression of H-EGF in rice suspension cells. (A) Schematic representation of the binary vector, pA8(+G+2TA)-SP-H-EGF, used for rice transformation. (B) PCR analysis of genomic DNA of T1 transgenic cell line, H-EGF 43. (C) RT-PCR analysis of the cell line, H-EGF 43. Untransformed wild-type rice cells (WT) and ddH2O was applied as negative controls. (D) Protein gel blot analysis of recombinant H-EGF produced in transformed rice cells. Total medium proteins secreted from sugar-starved rice cells, H-EGF 43, from 2-6 days were detected with anti-HSA polyclonal antibodies and anti-EGF antibodies, respectively. Total medium proteins were shown by a silver staining SDS-PAGE gel in the lowest panel. Arrow indicates the positions of H-EGF.

In addition, to improve the stability of the recombinant EGF protein, human serum albumin (HSA) was fused to N-terminal end of EGF to form recombinant HSA-EGF (called H-EGF). An expression cassette containing αAmy8(+G2TA) promoter (SEQ ID NO: 1) fused to the intron 1 of the maize ubiquitin gene (SEQ ID NO: 2), signal peptide sequence of αAmy3 gene (SEQ ID NO: 3), HSA fused with EGF (SEQ ID NO: 7) and 3' terminator region of the nopalin synthase gene (terminator) was constructed into an *agrobacterium* binary vector for transgenic rice transformation (FIG. 3A). The resultant recombinant construct was confirm to have the expression cassette comprising the nucleotide sequence of SEQ ID NO: 8 (pαAmy8(+G+2TA)+Ubi(intron)+SP+H-EGF) including the regulatory sequence (pαAmy8(+G+2TA)+Ubi(intron)+SP) being SEQ ID NO: 4. Several transgenic rice cell lines were obtained and suspension cultured cells were built up. Genomic DNAs, total RNAs were extracted from three milliliter of T1 rice suspension cell line, H-EGF 43, after sugar starvation for 3 days for genomic DNA (FIG. 3B) and total RNA for cDNA synthesis (FIG. 3C). Both PCR reactions were using HSA and Actin primer sets, including HSA-Forward (GGGCAT-GTTTTTGTATGAAT, SEQ ID NO: 12), HSA-Reverse (TTATAAGCCTAAGGCAGCTT, SEQ ID NO: 13), Actin-Forward (CTGATGGACAGGTTATCACC, SEQ ID NO: 14), Actin-Reverse (CAGGTAGCAATAGGTATTACAG, SEQ ID NO: 15). Here we showed that one transformed T1 cell line, H-EGF 43, contains the recombinant HSA DNA fragment (FIG. 3B) and cDNA (FIG. 3C). Then, this rice suspension cultured cell line, H-EGF 43, was cultured in medium lacking sucrose for 2-6 days, and cell cultured medium samples were collected. By western blot analysis with anti-EGF monoclonal antibodies and anti-HSA polyclonal antibodies, the results demonstrate that H-EGF proteins were stably existed in rice suspension cell cultured medium (FIG. 3D). Therefore, by using the expression system of the present invention, the recombinant EGF protein can be harvested from the culture medium, eliminating the need for protein extraction through cell lysis.

Figure 4:
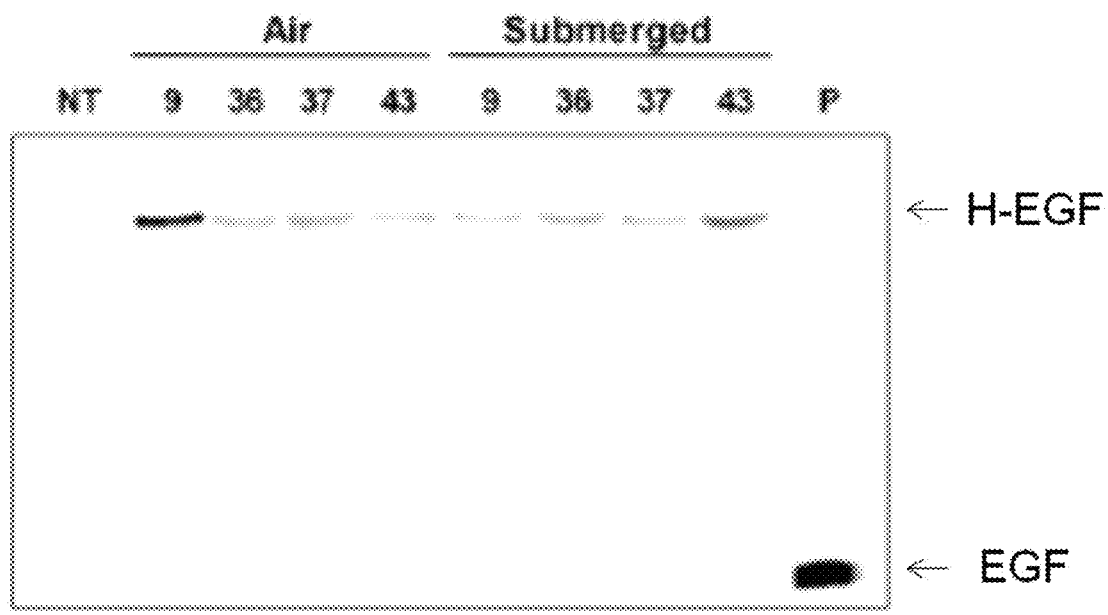
FIG. 4 shows that the H-EGF recombinant protein in aerobic (Air) and hypoxic (Submerged) transgenic seedlings by western blot analysis with an anti-EGF polyclonal antibody. P, commercial EGF was used as a positive control; NT, non-transgenic rice line. Arrow indicates the positions of H-EGF. Arrowhead indicates the positions of EGF.

Furthermore, to determine whether the αAmy8(+G+2TA) promoter could direct high-level accumulation of H-EGF in rice seedlings, T1 seeds of transgenic lines, H-EGF 9, 36, 37, and 43 carrying the αAmy8(+G+2TA):H-EGF gene were germinated and grown in air or under water (submerged) for 7 days; aerobic and hypoxic rice seedlings were collected and total soluble proteins were extracted. The results show that the H-EGF fusion proteins were detected in transgenic seedlings under both air and submerged conditions under the control of the αAmy8(+G+2TA) promoter of the invention (FIG. 4). The results confirm that the expression system of the present invention using the αAmy8(+G+2TA) promoter works in seedlings and the protein of interest as expressed can be harvested from seedlings by extraction.

2.5 EGF Bioactivity Assay

The binding of EGF receptor (EGFR) and its ligands leads to autophosphorylation of EGFR as well as subsequent activation of signal transduction pathways that are involved in regulating cellular proliferation. To determine whether recombinant H-EGF proteins secreted in rice cell cultured medium retain their biological properties, phosphorylation of EGFR in adenocarcinomic human alveolar basal epithelial cells, A549, was checked. A549 cells were cultured in Dulbecco's Modified Eagle Medium (DMEM)/F12 and supplemented with 10% fetal bovine serum and 100 units/mL gentamicin at 37° C. and 5% CO2 in 75-cm2 flasks. After A549 cells were reached concentration of $1 \times 10^6$, cell were starvation for 24 hours and stimulated with medium protein from rice cultivars TNG67 (WT) and from transformed rice cell line containing H-EGF for 10 minutes. Two hundred ng/ml Insulin-like growth factor 1 was applied as positive control (+), and without any treatment as a negative control (−). Results indicated that H-EGF secreted from transgenic rice cell line, H-EGF-43, could induce autophosphorylation of EGFR, as well as Insulin-like growth factor 1, a EGFR ligand protein (FIG. 5A), indicating that H-EGF produced by transgenic rice cells according to the present invention maintained the activity to activate EGFR.

Figure 5:
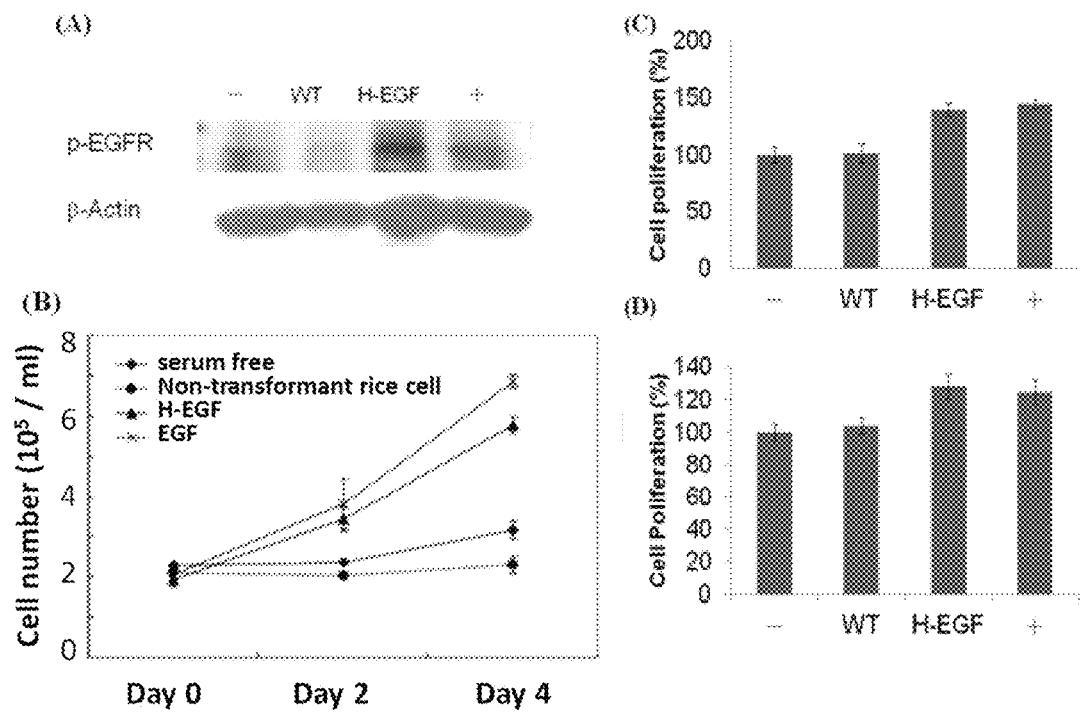
FIG. 5 shows that the bioactivity assay in mammalian cell lines for recombinant H-EGF secreted from transgenic rice cells. (A) Effect of recombinant H-EGF on the phosphorylation of EGF receptor (p-EGFR) in human A549 cells. Insulin-like growth factor 1 was applied as positive control (+). Both without any treatment (−) and rice wild-type non-transformant cell cultured medium (WT) were applied as negative controls. (B) Effect of recombinant H-EGF on the proliferation of HK-2 cells. Both serum free and Non-transformant rice cell were applied as native controls. Commercial EGF (labeled as EGF) was applied as positive control. The number of cells was determined on day 0, 2, and 4. (C) Effect of recombinant H-EGF on the cell proliferation of SH-SY5Y cells, human bone marrow neuroblastoma cell line. (D) Effect of recombinant H-EGF on the cell proliferation of L2 cells, rat lung epithelial cell line. Commercial EGF was applied as a positive control (+), and MS sugar free medium was applied as a negative control (−). Error bars indicate SE of 3 independent experiments performed in triplicate.

Next, HK-2 cell proliferation assay was employed (Sarkozi et al. (2007) *J Cell Physiol* 211 (1):88-100). The proliferation of HK-2 cells, an immortalized proximal tubule cell line derived from normal adult human kidney (Ryan et al. (1994) *Kidney Int* 45:48-57), can be induced by growth promoting factors such as EGF (Haussler et al. (2005) *Am J Physiol Renal Physiol* 289 (4):F808-815. doi:00434.2003; Sarkozi et al. (2007) supra). HK-2 cells were cultured in serum free medium lacking growth factors for 48 h and then treated with growth factors for additional 2 and 4 days, and the number of cells was determined. When serum and growth factor-starved HK-2 cells were supplemented with 150 ng/ml total rice cell cultured medium protein of cell line (5 ng H-EGF), a 2.9-fold increase in cell proliferation was resulted, which was similar to that induced by 5 ng/ml of commercial EGF (FIG. 5B). Same treatment was applied into SH-SY5Y cells which are derived from human bone marrow neuroblastoma cells, and results showed no difference in cell proliferation between H-EGF and commercial EGF (FIG. 5C). The rat lung epithelial cell line, L2, also indicates the same result that the recombinant H-EGF secreted from rice suspension cultured cells according to the invention possesses biological activity comparable to that of the commercial EGF (FIG. 5D).

In summary, we created the αAmy8(+G+2TA) promoter with strong activity for the high-level expression of recombinant proteins in rice cells and germinated seedlings. We also established an EGF expression system in rice suspension cells by constructing a nucleotide sequence encoding an EGF fusion protein operatively linked to a single peptide sequence under control of the αAmy8(+G+2TA) promoter, in which bio-active recombinant EGF fusion protein is stably expressed and secreted into culture medium, eliminating the need for protein extraction through cell lysis, which provides an economic and efficient process for EGF production.

It is generally believed that persons skilled in the art of the present invention should be able to utilize the present invention to its broadest scope based on the descriptions herein without further illustration. Therefore, it should be understood that the descriptions and claims provided herein are for illustration only but do not in any way limit the scope of the present invention.

Sequence Information

```
SEQ ID NO: 1 (pαAmy8(+G+2TA))
cggaggactagcgaagaatactgcagctggggttggcgctgctaatgaccaacgtttgatcattcgttttatttattttttttgtaaatatg aaaatatttatgtcatgtttaaaagaacatttgatgatgaatcaagtcacaataaaagaaaaaataattgcataatttttttaaataaaaaga atgatcaaacgttaaacaaaaagtcaacgtcatacattaaaacataaaagttagtataattcaaagatatggatgaaggtcacaagca atgcgcttgacgtggtgcaaatctggagttattgagctttccattgcatgtctgtgattttaccaagtcaatcgacgtttgctgttttctttgc aaatagtcctagactaagttacttgcagttgcaggattatggtggattggtgacggagttggtgcttatggcctttgttttctgtcagggg agttgtctgctctgcaggtcatataaactctgtaaaagtgtatattggcatttcgtcgatgaaatgggagaggatctcctctcttttttcaat aaaaaaagtaaatgcaaaatatatgtccgttgcaccgatctcctttccaaaaccgaaagtttccctgccggcgcttgatccgtcacacc gatgacgcgacgccggtagaggcccggtacctgttcgaacaaccaactgatgtgcggctcctccgcttgcggcttgcctcttatcaa cgtatcgcgaattcccgggtgcgtgatcggtgatcgatcaccgagagagaccggacgacgagtcgagagagctcgcgcgcgcct cgatcggcgcggcggtgactcgacctacgtggcaagtagctgcacggctcaaggcggcactccatcaccggacaccggggtcc
                          G-box agactactcgtttccgttggagaaataaccatccttatccatatccacgccccgggaattgcaacagcattgattgttgatatctaattcg
                                   TA box Cctcggccatgtaacctccgacctgatcctcttggacactataaatagaggccagttcaggcaatgcaagagcagagaagcagag tcgaccaggcagctcttcttctctttgcgaaggttggctacttggccagccattaggaaacaagttagtttggagaagaagcagagtt gagactgcatttgcat SEQ ID NO: 2 (Ubi(intron))
agatctcccccaaatccaccgtcggcacctccgcttcaaggtacgccgctcgtcctcccccccccccctctctaccttctctagat cggcgttccggtccatggttagggcccggtagttctacttctgttcatgtttgtgttagatccgtgtttgtgttagatccgtgctgctagcg ttcgtacacggatgcgacctgtacgtcagacacgttctgattgctaacttgccagtgtttctctttggggaatcctgggatggctctagc cgttccgcagacgggatcgatttcatgattttttttgtttcgttgcataggggtttggtttgccctttcttttattttcaatatatgccgtgcactt
```

-continued gtttgtcgggtcatcttttcatgcttttttttgtcttggttgtgatgatgtggtctggttgggcggtcgttctagatcggagtagaattctgttt caaactacctggtggatttattaattttggatctgtatgtgtgtgccatacatattcatagttacgaattgaagatgatggatgaaatatc gatctaggataggtatacatgttgatgcgggttttactgatgcatatacagagatgcttttgttcgcttggttgtgatgatgtggtgtggtt gggcggtcgttcattcgttctagatcggagtagaatactgtttcaaactacctggtgtatttattaattttggaactgtatgtgtgtgtcata catcttcatagttacgagtttaagatggatggaaatatcgatctaggataggtatacatgttgatgtgggttttactgatgcatatacatga tggcatatgcagcatgctattcatatgctctaaccttgagtacctatctattataataaacaagtatgttttataattattttgatcttgatatact tggatgatggcatatgcagcagctatatgtggattttttagccctgccttcatacgctatttatttgcttggtactgtttcttttgtcgatgct caccctgttgtttggtgttacttctgca SEQ ID NO: 3 (SP)
atgaagaacaccagcagcttgtgtttgctgctcctcgtggtgctctgcagcttgacctgtaactcgggtcaagcacaggtcct cttcgataagctt SEQ ID NO: 4 (pαAmy8(+G+2TA)+Ubi+SP)
cggaggactagcgaagaatactgcagctggggttggcgctgctaatgactaacgtttgatcattcgttttattttctttttttg taaatatgaaaatatttatgtcatgtttaaagaacatttgatgatgaatcaagtcacaataaaagaaaaaataattgcata atttttttaaataaaaagaatgatcaaacgttaaacaaaaagtcaacgtcatacattaaaacataaaagttagtataattc aaagatatggatgaaggtcacaagcaatgcgtttgacgtggtgcaaatctggagttattgagcttttccattgcatgtctgtg attttaccaagtcaatcgacgtttgctgttttctttgcaaatagtcctagactaagttacttgcagttgcaggattatggtggat tggtgacggagttggtgcttatggcctttgttttctgtcaggggagttgtctgctctgcaggtcatataaactctgtaaaagtg tatattggcatttcgtcgatgaaatgggagaggatctcctctcttttttcaataaaaaaagtaaatgcaaatatatgtccg ttgcaccgatctccttttccaaaccgaaagtttccctgccggcgcttgatccgtcacaccgatgacgcgacgccggtagagg cccggtacctgttcgaacaaccaactgatgtgcggctcctccgcttgcggcttgcctcttatcaacgtatcgcgaattcccgg gtgcgtgatcggtgatcgatcaccgagagagaccggacgacgagtcgagagagctcgcgcgcgcctcgatcggcgcggc ggtgactcgacctacgtggcaagtagctgcacggctcaaggcggcactccatcaccggacaccggggtccagactactcg tttccgttggagaaataaccatccttatccatatccacgccccgggaattgcaacagcattgattgttgatatctaattcgcct cggccatgtaacctccgacctgatcctcttggacactataaatagaggccagttcaggcaatgcaagagcagagaagcag agtcgaccaggcagctcttcttctctttgcgaaggttggctacttggccagccattaggaaacaagttagtttggagaagaa gcagagttgagactgcatttgcatagatctcccccaaatccaccccgtcggcacctccgcttcaaggtacgccgctcgtcctc ccccccccccctctctaccttctctagatcggcgttccggtccatggttagggcccggtagttctacttctgttcatgtttgtg ttagatccgtgtttgtgttagatccgtgctgctagcgttcgtacacggatgcgacctgtacgtcagacacgttctgattgctaa cttgccagtgtttctctttggggaatcctgggatggctctagccgttccgcagacgggatcgatttcatgatttttttgtttcgt tgcatagggtttggtttgccctttttcctttatttcaatatatgccgtgcacttgtttgtcgggtcatcttttcatgcttttttttgtct tggttgtgatgatgtggtctggttgggcggtcgttctagatcggagtagaattctgtttcaaactacctggtggatttattaat tttggatctgtatgtgtgtgccatacatattcatagttacgaattgaagatgatggatgaaatatcgatctaggataggtat acatgttgatgcgggttttactgatgcatatacagagatgcttttgttcgcttggttgtgatgatgtggtgtggttgggcggt cgttcattcgttctagatcggagtagaatacgtttcaaactacctggtgtatttattaattttggaactgtatgtgtgtgtcat acatcttcatagttacgagtttaagatggatggaaatatcgatctaggataggtatacatgttgatgtgggttttactgatgc atatacatgatggcatatgcagcatctattcatatgctctaaccttgagtacctatctattataataaacaagtatgttttata attattttgatcttgatatacttggatgatggcatatgcagcagctatatgtggattttttagccctgccttcatacgctattta tttgcttggtactgtttcttttgtcgatgctcaccctgttgtttggtgttacttctgcagactagtttacacagatatgaagaaca ccagcagcttgtgtttgctgctcctcgtggtgctctgcagcttgacctgtaactcgggtcaagcacaggtcctcttcgataag ctt

SEQ ID NO: 5 (EGF)
NSDSECPLSHDG YCLHDGVCMY IEALDKYACNCVVGYIGERC

QYRDLKWWEL R

SEQ ID NO: 6 (HSA)
DAH KSEVAHRFKD LGEENFKALVLIAFAQYLQQ CPFEDHVKLV

NEVTEFAKTC VADESAENCD KSLHTLFGDK LCTVATLRETYGEMADCCAK

QEPERNECFL QHKDDNPNLP RLVRPEVDVM CTAFHDNEET

FLKKYLYEIARRHYPYFYAPE LLFFAKRYKA AFTECCQAAD KAACLLPKLD

ELRDEGKASS AKQRLKCASLQKFGERAFKA WAVARLSQRF PKAEFAEVSK

LVTDLTKVHT ECCHGDLLEC ADDRADLAKYICENQDSISS KLKECCEKPL

LEKSHCIAEV ENDEMPADLP SLAADFVESK DVCKNYAEAKDVFLGMFLYE

YARRHPDYSV VLLLRLAKTY ETTLEKCCAA ADPHECYAKV

FDEFKPLVEEPQNLIKQNCE LFEQLGEYKF QNALLVRYTK KVPQVSTPTL

VEVSRNLGKV GSKCCKHPEAKRMPCAEDYL SVVLNQLCVL HEKTPVSDRV

TKCCTESLVN RRPCFSALEV DETYVPKEFNAETFTFHADI CTLSEKERQI

KKQTALVELV KHKPKATKEQ LKAVMDDFAA

FVEKCCKADDKETCFAEEGK KLVAASQAAL GL

SEQ ID NO: 7 (H-EGF)
gatgcacacaagagtgaggttgctcatcggtttaaagatttgggagaagaaaatttcaaagccttggtgttgattgcctttgct cagtatcttcagcagtgtccatttgaagatcatgtaaaattagtgaatgaagtaactgaatttgcaaaaacatgtgttgctgatg agtcagctgaaaattgtgacaaatcacttcatacccttttggagacaaattatgcacagttgcaactcttcgtgaaacctatgg tgaaatggctgactgctgtgcaaaacaagaacctgagagaaatgaatgcttcttgcaacacaaagatgacaacccaaacct cccccgattggtgagaccagaggttgatgtgatgtgcactgcttttcatgacaatgaagagacatttttgaaaaaatacttatat gaaattgccagaagacatcctttattttatgccccggaactccttttctttgctaaaaggtataaagctgcttttacagaatgttg ccaagctgctgataaagctgcctgcctgttgccaaagctcgatgaacttcgggatgaagggaaggcttcgtctgccaaaca gagactcaagtgtgccagtctccaaaaatttggagaaagagctttcaaagcatgggcagtagctcgcctgagccagagatt tcccaaagctgagtttgcagaagtttccaagttagtgacagatcttaccaaagtccacacggaatgctgccatggagatctgc ttgaatgtgctgatgatgacagggcggaccttgccaagtatatctgtgaaaatcaagattcgatctccagtaaactgaaggaatgc tgtgaaaaacctctgttggaaaaatcccactgcattgccgaagtggaaaatgatgagatgcctgctgacttgccttcattagct gctgattttgttgaaagtaaggatgtttgcaaaaactatgctgaggcaaaggatgtcttcctgggcatgtttttgtatgaatatgc aagaaggcatcctgattactctgtcgtgctgctgctgagacttgccaagacatatgaaaccactctagagaagtgctgtgcc gctgcagatcctcatgaatgctatgccaaagtgttcgatgaatttaaacctcttgtggaagagcctcagaatttaatcaaacaa aattgtgagcttttttgagcagcttggagagtacaaattccagaatgcgctattagttcgttacaccaagaaagtaccccaagtg tcaactccaactcttgtagaggtctcaagaaacctaggaaaagtgggcagcaaatgttgtaaacatcctgaagcaaaaaga atgccctgtgcagaagactatctatccgtggtcctgaaccagttatgtgtgttgcatgagaaaacgccagtaagtgacagagt caccaaatgctgcacagaatccttggtgaacaggcgaccatgcttttcagctctggaagtcgatgaaacatacgttcccaaa gagtttaatgctgaaacattcaccttccatgcagatatatgcacactttctgagaaggagagacaaatcaagaaacaaactgc acttgttgagctcgtgaaacacaagcccaaggcaacaaaagagcaactgaaagctgttatggatgatttcgcagcttttgta gagaagtgctgcaaggctgacgataaggagacctgctttgccgaggagggtaaaaaacttgttgctgcaagtcaagctgc cttaggcttaggatccatcgagggccgcaactccgactccgagtgcccgctctcccacgacggctactgcctccacgacg gcgtgtgcatgtacatcgaggcccctcgacaagtacgcctgcaactgcgtggtgggctacatcggcgagcgctgccagtac cgcgacctcaagtggtgggagctccgc SEQ ID NO: 8 (pαAmy8(+G+2TA)+Ubi(intron)+SP+HSA-EGF)
cggaggactagcgaagaatactgcagctgggggttggcgctgctaatgaccaacgtttgatcattcgttttattttttttttgtaaatatg aaaatatttatgtcatgtttaaagaacatttgatgatgaatcaagtcacaataaaagaaaaaataattgcataattttttttaaataaaaaga atgatcaaacgttaaacaaaaagtcaacgtcatacattaaaacataaaagttagtataattcaaagatatggatgaaggtcacaagca atgcgcttgacgtggtgcaaatctggagttattgagctttccattgcatgtctgtgattttaccaagtcaatcgacgtttgctgttttctttgc aaatagtcctagactaagttacttgcagttgcaggattatggtggattggtgacggagttggtgcttatggcctttgttttctgtcaggg agttgtctgctctgcaggtcatataaactctgtaaaagtgtatattggcatttcgtcgatgaaatgggagaggatctcctctcttttttcaat aaaaaaaagtaaatgcaaaatatatgtccgttgcaccgatctcctttccaaaccgaaagtttccctgccggcgcttgatccgtcacacc gatgacgcgacgccggtagaggcccggtacctgttcgaacaaccaactgatgtgcggctcctccgcttgcggcttgcctcttatcaa cgtatcgcgaattcccgggtgcgtgatcggtgatcgatcaccgagagagagaccggacgacgagtcgagagagctcgcgcgcgcct cgatcggcgcggcggtgactcgacctacgtggcaagtagctgcacggctcaaggcggcactccatcaccggacaccggggtcc agactactcgtttccgttggagaaataaccatccttatccatatccacgccccgggaattgcaacagcattgattgttgatatctaattcg cctcggccatgtaacctccgacctgatcctcttggacactataaatagaggccagttcaggcatttgcaagagcagagaagcagagt cgaccaggcagctcttcttctctttgcgaaggttggctacttggccagccattaggaaacaagttagtttggagaagaagcagagttg agactgcatttgcatagatctcccffaaatccaccgtcggcacctccgcttcaaggtacgcgctcgtcctccccccccccccctct ctaccttctctagatcggcgttccggtccatggttagggcccggtagttctacttctgttcatgtttgtgttagatccgtgtttgtgttagat ccgtgctgctagcgttcgtacacggatgcgacctgtacgtcagacacgttctgattgctaacttgccagtgtttctctttgggggaatcct gggatggctctagccgttccgcagacgggatcgatttcatgatttttttgtttcgttgcataggggtttggtttgccctttcctttatttcaat atatgccgtgcacttgtttgtcgggtcatctttcatgctttttttgtcttggttgtgatgatgtggtctggttgggcggtcgttctagatcgg agtagaattctgtttcaaactacctggtggatttattaattttggatctgtatgtgtgtgccatacatattcatagttacgaattgaagatgat ggatggaaatatcgatctaggataggtatacatgttgatgcgggttttactgatgcatatacagagatgcttttttgttcgcttggttgtgat gatgtggtgtggttgggcggtcgttcattcgttctagatcggagtagaatactgtttcaaactacctggtgtatttattaattttggaactgt atgtgtgtgtcatacatcttcatagttacgagtttaagatggatggaaatatcgatctaggataggtatacatgttgatgtgggttttactg atgcatatacatgatggcatatgcagcatctattcatatgctctaaccttgagtacctatctattataataaacaagtatgttttataattattt tgatcttgatatacttggatgatggcatatgcagcagctatatgtggattttttttagccctgccttcatacgctatttatttgcttggtactgtt tcttttgtcgatgctcaccctgttgtttggtgttacttctgcagactagtttacacagatatgaagaacaccagcagcttgtgtttgctgctc ctcgtggtgctctgcagcttgacctgtaactcgggtcaagcacaggtcctcttcgataagcttgatgcacacaagagtgaggttgctc atcggtttaaagatttgggagaagaaaatttcaaagccttggtgttgattgcctttgctcagtatcttcagcagtgtccatttgaagatcat gtaaaattagtgaatgaagtaactgaatttgcaaaaacatgtgttgctgatgagtcagctgaaaattgtgacaaatcacttcataccctt ttggagacaaattatgcacagttgcaactcttcgtgaaacctatggtgaaatggctgactgctgtgcaaaacaagaacctgagagaa atgaatgcttcttgcaacacaaagatgacaacccaaacctcccccgattggtgagaccagaggttgatgtgatgtgcactgcttttcat gacaatgaagagacatttttgaaaaaatacttatatgaaattgccagaagacatccttacttttatgccccggaactccttttctttgctaa aaggtataaagctgcttttacagaatgttgccaagctgctgataaagctgcctgcctgttgccaaagctcgatgaacttcgggatgaa gggaaggcttcgtctgccaaacagagactcaagtgtgccagtctccaaaaatttggagaaagagctttcaaagcatgggcagtagc tcgcctgagccagagatttcccaaagctgagtttgcagaagtttccaagttagtgacagatcttaccaaagtccacacggaatgctgc catggagatctgcttgaatgtgctgatgacagggcggaccttgccaagtatatctgtgaaaatcaagattcgatctccagtaaactga aggaatgctgtgaaaaacctctgttggaaaaatcccactgcattgccgaagtggaaaatgatgagatgcctgctgacttgccttcatt agctgctgattttgttgaaagtaaggatgtttgcaaaaactatgctgaggcaaaggatgtcttcctgggcatgttttttgtatgaatatgca agaaggcatcctgattactctgtcgtgctgctgctgagacttgccaagacatatgaaaccactcgagagaagtgctgtgccgctgca gatcctcatgaatgctatgccaaagtgttcgatgaatttaaacctcttgtggaagagcctcagaatttaatcaaacaaaattgtgagcttt ttgagcagcttggagagtacaaaattccagaatgcgctattagttcgttacaccaagaaagtaccccaagtgtcaactccaactcttgta gaggtctcaagaaacctaggaaaagtgggcagcaaatgttgtaaacatcctgaagcaaaagaatgccctgtgcagaagactatct atccgtggtcctgaaccagttatgtgtgtgttgcatgagaaacgccagtaagtgacagagtcagagtcaccaaatgctgcacagaatccttggt gaacaggcgaccatgcttttcagctctggaagtcgatgaaacatacgttcccaaagagtttaatgctgaaacattcaccttccatgca gatatatgcacactttctgagaaggagagacaaatcaagaaacaaactgcacttgttgagctcgtgaaacacaagcccaaggcaac aaaagagcaactgaaagctgttatggatgatttcgcagcttttgtagagaagtgctgcaaggctgacgataaggagacctgctttgcc gaggagggtaaaaaacttgttgctgcaagtcaagctgccttaggcttaggatccatcgagggccgcaactccgactccgagtgccc gctctcccacgacggctactgcctccacgacggcgtgtgcatgtgacatcgaggccctcgacaagtacgcctgcaactgcgtggtg ggctacatcggcgagcgctgccagtaccgcgacctcaagtggtgggagctccgc

---

What is claimed is:

1. An engineered promoter, comprising the sequence as set forth in SEQ ID NO: 1.

2. A recombinant construct, comprising an expression cassette which comprises a regulatory sequence, operatively linked to a nucleotide sequence encoding a polypeptide, wherein the regulatory sequence comprises the promoter of claim 1.

3. The recombinant construct of claim 2, wherein the regulatory sequence further comprises a ubiquitin (Ubi) intron sequence.

4. The recombinant construct of claim 3, wherein the Ubi intron sequence has the sequence of SEQ ID NO: 2.

5. The recombinant construct of claim 2, wherein the regulatory sequence further comprises a nucleotide sequence encoding a signal peptide sequence.

6. The recombinant construct of claim 5, wherein the nucleotide sequence encoding the signal peptide sequence has the sequence of SEQ ID NO: 3.

7. The recombinant construct of claim 2, wherein the regulatory sequence has the sequence of SEQ ID NO: 4.

8. The recombinant construct of claim 2, wherein the polypeptide is an epidermal growth factor (EGF).

9. The recombinant construct of claim 2, wherein the polypeptide is a fusion polypeptide comprising an epidermal growth factor (EGF) fused to a human serum albumin (HSA).

10. The recombinant construct of claim 9, wherein the nucleotide sequence encoding the fusion polypeptide has the sequence of SEQ ID NO: 7.

11. The recombinant construct of claim 2, wherein the expression cassette has the sequence of SEQ ID NO: 8.

12. A transformed cell or a transgenic plant comprising the recombinant construct of claim 2.

13. A method for producing a foreign polypeptide comprising
  (a) culturing a cell transformed with the recombinant construct of claim 2 under a condition for expression of the polypeptide of interest; and
  (b) recovering the polypeptide from the cell culture.

14. The method of claim 13, wherein in step (a) the cell is a plant cell.

15. The method of claim 14, wherein in step (a) the plant cell is cultured and suspension culture is obtained, and in step (b) the polypeptide is recovered from the suspension culture.

16. The method of claim 15, wherein in step (a), the plant cell is cultured in a sugar deficient condition.

17. The method of claim 16, wherein in step (b) the suspension culture is subjected to filtration and the medium is collected to recover the polypeptide.

18. A method for producing a foreign polypeptide comprising
  (a) growing a transgenic plant containing the recombinant construct of claim 2 under a condition suitable for expression of the polypeptide of interest; and
  (b) recovering the polypeptide from the transgenic plant.

19. The method of claim 18, wherein in step (a) the transgenic plant is rice.

20. The method of claim 18, wherein in step (b) the polypeptide is recovered by extracting the transgenic plant.

* * * * *